US012692531B2

(12) United States Patent
Schum et al.

(10) Patent No.: US 12,692,531 B2
(45) Date of Patent: Jul. 28, 2026

(54) CURING SYSTEM AND METHOD FOR CURING PRESSURE-SENSITIVE ADHESIVE APPLIED TO PRODUCTS

(71) Applicant: MJR Vision LLC, Cherry Hill, NJ (US)

(72) Inventors: Michael Schum, Cherry Hill, NJ (US); Heriberto Medina, NW Palm Bay, FL (US)

(73) Assignee: MJR Vision LLC, Cherry Hill, NJ (US)

( * ) Notice: Subject to any disclaimer, the term of this patent is extended or adjusted under 35 U.S.C. 154(b) by 14 days.

(21) Appl. No.: 18/854,124

(22) PCT Filed: Jul. 12, 2023

(86) PCT No.: PCT/US2023/027479
§ 371 (c)(1),
(2) Date: Oct. 4, 2024

(87) PCT Pub. No.: WO2024/015435
PCT Pub. Date: Jan. 18, 2024

(65) Prior Publication Data
US 2025/0353317 A1 Nov. 20, 2025

Related U.S. Application Data

(60) Provisional application No. 63/388,775, filed on Jul. 13, 2022.

(51) Int. Cl.
B30B 7/02 (2006.01)
B30B 7/04 (2006.01)
(Continued)

(52) U.S. Cl.
CPC ................ C12Q 1/18 (2013.01); B30B 7/023 (2013.01); B30B 7/04 (2013.01); B42C 9/00 (2013.01)

(58) Field of Classification Search
CPC ...... C12Q 1/18; G01N 2560/00; B30B 7/023; B30B 7/04; B42C 9/00
(Continued)

(56) References Cited

U.S. PATENT DOCUMENTS 3,731,617 A 5/1973 Hall
5,641,370 A * 6/1997 Sanko ..................... B32B 39/00
156/228
(Continued)

FOREIGN PATENT DOCUMENTS

EP 0791478 A1 8/1997
EP 1437233 B1 7/2004
EP 3134272 B1 12/2017

*Primary Examiner* — James D Sells
(74) *Attorney, Agent, or Firm* — Volpe Koenig

(57) ABSTRACT

The present disclosure provides a compact curing assembly that receives folded and glued booklets for storing these booklets under pressure and subsequently feeds these booklets to a post-processor (i.e. inspection system) after each booklet is completely cured. A first pressure plate can keep stacked booklets under pressure as newly input booklets or products enter the curing assembly and push the entire stack of booklets. A second pressure plate can apply pressure to a trailing edge of the stacked booklets as the booklets are discharged from the curing assembly.

22 Claims, 17 Drawing Sheets

(51) Int. Cl.
    *B42C 9/00*        (2006.01)
    *C12Q 1/18*        (2006.01)

(58) Field of Classification Search
    USPC ........................................................ 156/580
    See application file for complete search history.

(56)                References Cited

U.S. PATENT DOCUMENTS

| | | |
|---|---|---|
| 2007/0286705 A1 | 12/2007 | Sasamoto et al. |
| 2010/0298972 A1 | 11/2010 | Schum |
| 2013/0259607 A1 | 10/2013 | Nakanishi et al. |
| 2018/0016211 A1 | 1/2018 | Gribkov et al. |

\* cited by examiner

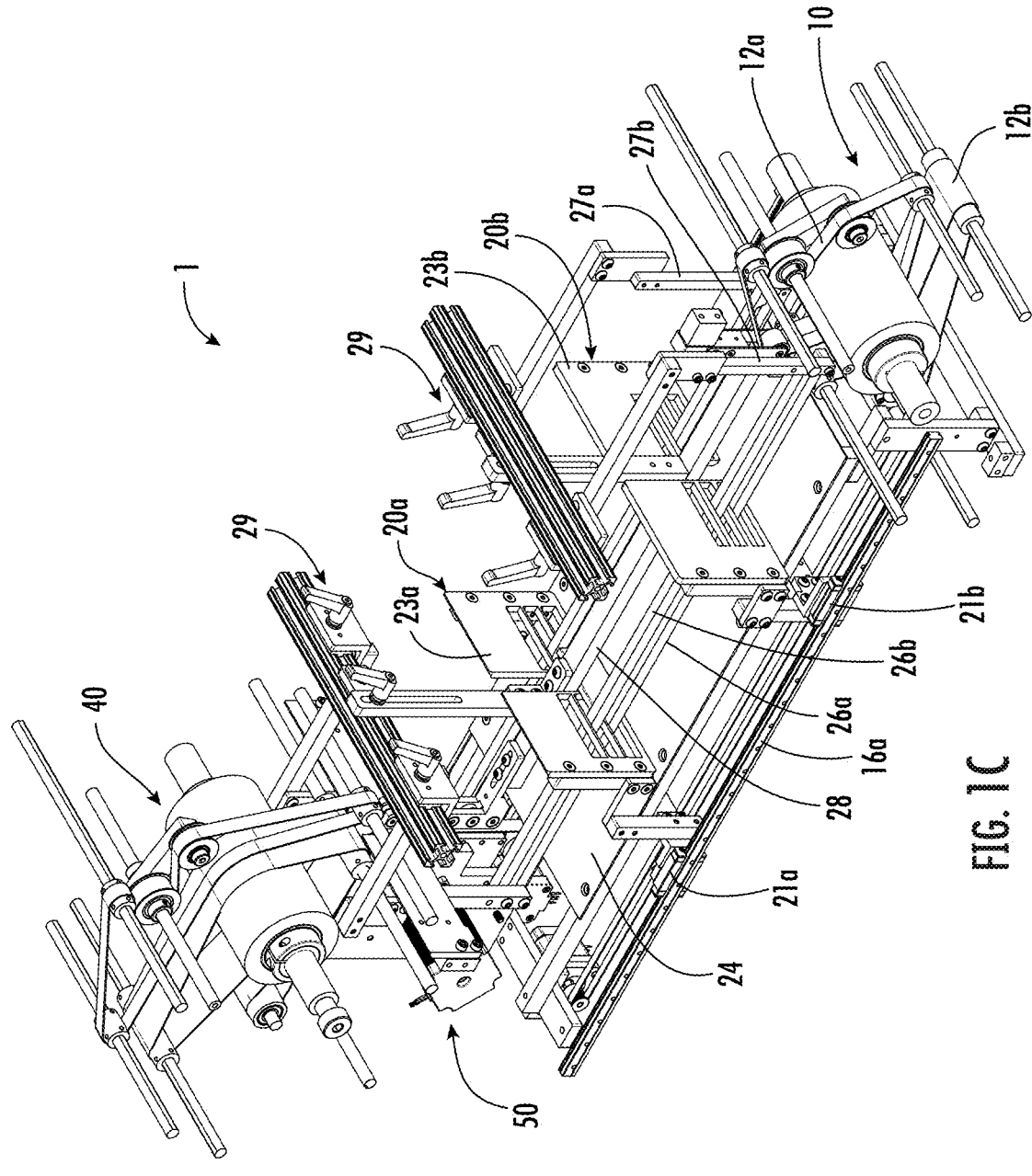
FIG. IC

52c

52d

52a

52b

52c

52b

52d

52e

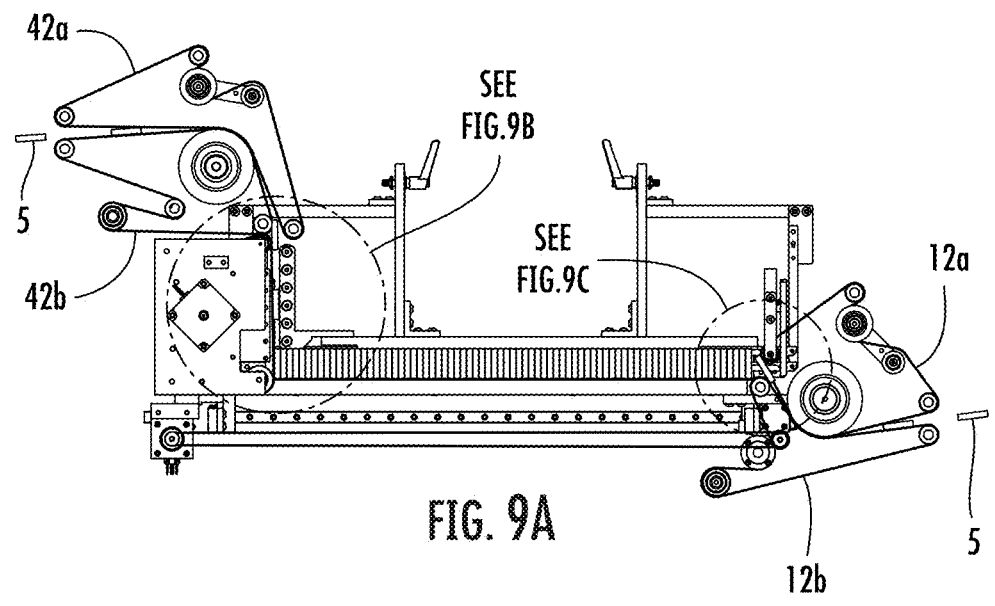
FIG. 9A
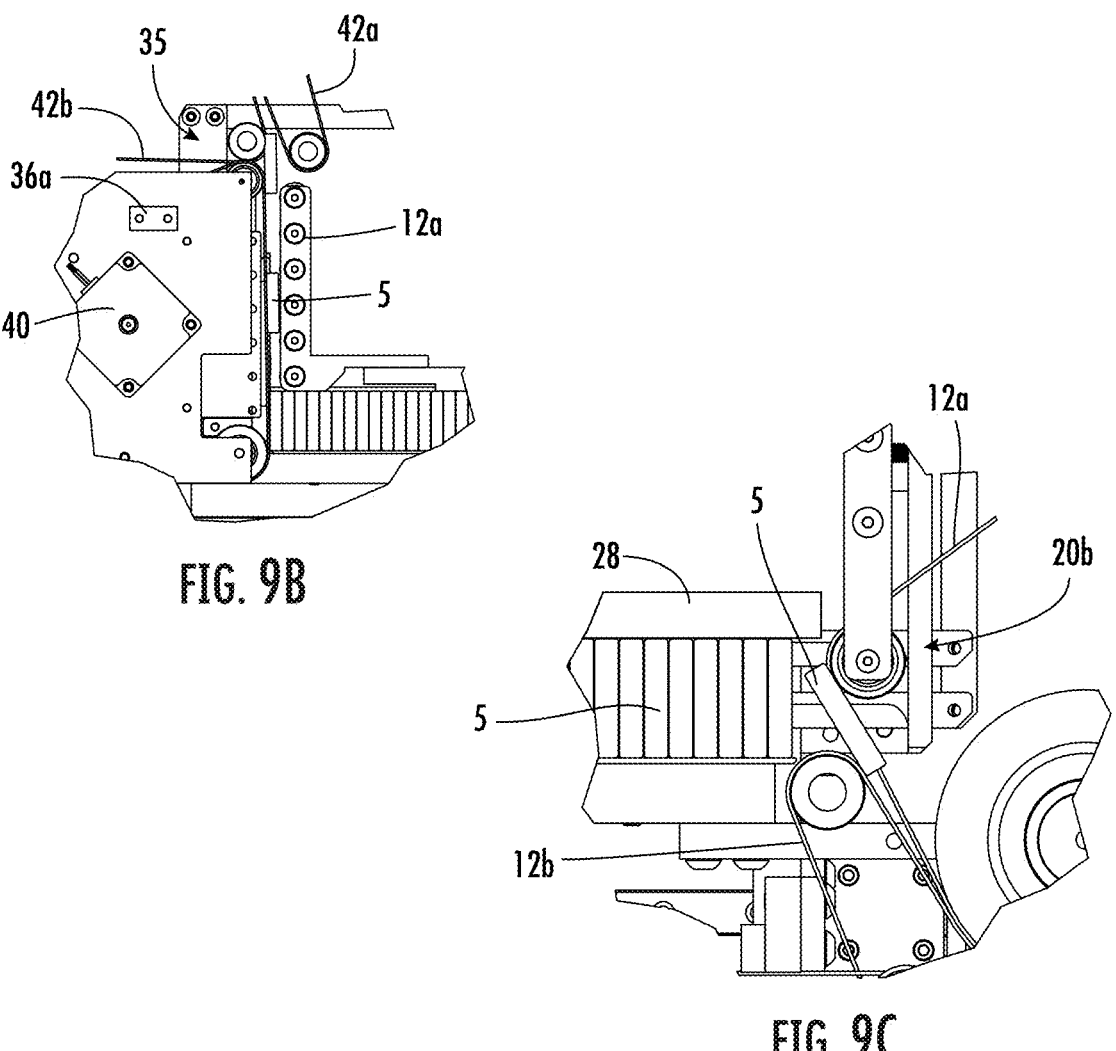
FIG. 9B
FIG. 9C

CURING SYSTEM AND METHOD FOR CURING PRESSURE-SENSITIVE ADHESIVE APPLIED TO PRODUCTS

CROSS-REFERENCE TO RELATED APPLICATIONS

This application claims priority from U.S. Provisional Application No. 63/388,775, filed Jul. 13, 2022, which is incorporated herein by reference as if fully set forth.

FIELD OF INVENTION

The present disclosure relates to a curing system for use with products having pressure-sensitive adhesive, and a method of applying pressure to a product having pressure-sensitive adhesive.

BACKGROUND

There are many applications where folded sheets of information, such as pharmaceutical literature, requires an adhesive applicator to be used in the final fold of the folding process to form a folded booklet, commonly called an outsert. Thus, the frequently used pressure-sensitive adhesive requires some time under pressure for curing before the folded outsert can be moved downstream for packing or transported to an inspection module or system.

One issue that commonly arises is the inability to inspect the booklet without applying the pressure from both sides of the booklet until the booklet or outsert is fully dry. Typically, in manual operation, an operator waits about 12-15 seconds before manually removing and visually inspecting several outserts at a time. In automatic operation, the inspection is achieved by a camera system while the outsert is held under pressure from two sides and thus, still unable to completely determine the status of the curing process due to inability to view the product in an unobstructed manner.

One solution to overcome this problem requires integrating a relatively longer conveying system. Although such systems may provide a favorable result, the footprint of these systems is too large and therefore is undesirable.

It would be desirable to provide a relatively compact, reliable, and efficient curing assembly.

SUMMARY

A curing assembly is disclosed herein that provides an improved arrangement for curing adhesive that is applied to products. The products can be held within a product stack, which can include a plurality of booklets or outserts with a pressure-sensitive adhesive or glue applied thereon.

The curing assembly can include a track assembly, a first pressure plate assembly attached to the track assembly, and a second pressure plate assembly attached to the track assembly. A control assembly can be configured to selectively drive the first pressure plate assembly and the second pressure plate assembly along the track assembly during various operating states and conditions. The control assembly can include a variety of components, such as timing belts, motors, user interfaces (i.e. monitors, computers, keyboards, etc.).

The products are configured to be fed to the curing assembly such that the products are stacked against one another to form a product stack. The first pressure plate assembly is configured to apply a first predetermined pressure to a leading edge of the product stack at least during an initial stage of an accumulating state, and the second pressure plate assembly is configured to apply a second predetermined pressure to a trailing edge of the product stack at least during final stage of an output state. The first and second predetermined pressures can be identical or can be different from each other. The first and second predetermined pressures can each preferably be within a predetermined range, which can be based on multiple factors, such as the type of adhesive, type of material, or type of fold.

The first pressure plate assembly can be considered a front or foremost plate assembly, and the second pressure plate assembly can be considered a rear plate assembly, in one configuration. One of ordinary skill in the art would understand that the relative orientation or direction of these components can vary.

The first pressure plate assembly can be driven by the control assembly out of contact with the product stack during the output state. The second pressure plate assembly can be positioned away from the product stack during the accumulating state.

An overhead guide assembly can be configured to engage an upper portion of the product stack. The overhead guide assembly can provide an upper limit for the direction of travel of products as the products are input to the curing assembly. A height of the overhead guide assembly can be adjustable. A side guide assembly can be configured to guide lateral portions of the product stack as the products are fed through the curing assembly. A width of the side guide assembly can be adjustable. One of ordinary skill in the art would understand that the system disclosed herein can be used for products of varying dimensions.

A discharge assembly can include at least one discharge belt, and the at least one discharge belt can be configured to engage the leading edge of the product stack during the output state. The discharge assembly can be generally configured to drive the products away from the product stack and downstream for inspection and further processing.

In one configuration, the output state can begin when the first pressure plate assembly is driven out of contact with the product stack and the at least one discharge belt can begin engaging the leading edge of the product stack to discharge products from the curing assembly. The accumulating state can be at least 20 seconds. One of ordinary skill in the art would understand that the duration of this state can vary.

The first pressure plate assembly and the second pressure plate assembly can each include a plate arranged in a parallel direction relative to the product stack. The first pressure plate assembly and the second pressure plate assembly can include various other features, such as carriages, mounting frames, etc.

In one configuration, only one of the first pressure plate assembly and the second pressure plate assembly is engaged with the product stack in both the accumulating state and the output state. One of ordinary skill in the art would understand based on this disclosure that both plate assemblies can be positioned away from the product stack, and the accumulating and output states can occur at the same time or overlap with each other.

A method of applying pressure to products for curing adhesive is also disclosed herein. The method can include generally using the curing assembly described herein. The method can include (i) feeding or inputting the products to a curing assembly to form a product stack; (ii) engaging a leading edge of the product stack with a first pressure plate assembly at least during an initial stage of an accumulating state such that a first predetermined pressure is applied to the product stack; (iii) engaging a trailing edge of the product stack with a second pressure plate assembly at least during a final stage of an output state such that a second predetermined pressure is applied to the product stack; and (iv) discharging the products from the curing assembly. Various other steps can be included in the method. Additionally, the method steps described herein can be coterminous with each other.

Additional embodiments are disclosed herein.

BRIEF DESCRIPTION OF THE DRAWINGS

The foregoing Summary and the following Detailed Description will be better understood when read in conjunction with the appended drawings, which illustrate a preferred embodiment of the disclosure. In the drawings:

FIG. 1C is another top perspective view of the curing assembly.

FIG. 9A is a side view of the curing assembly during the output state.

FIG. 9B is a magnified view of a first region of FIG. 9A.

FIG. 9C is a magnified view of a second region of FIG. 9A.

DETAILED DESCRIPTION OF THE PREFERRED EMBODIMENTS

Figure 1A:
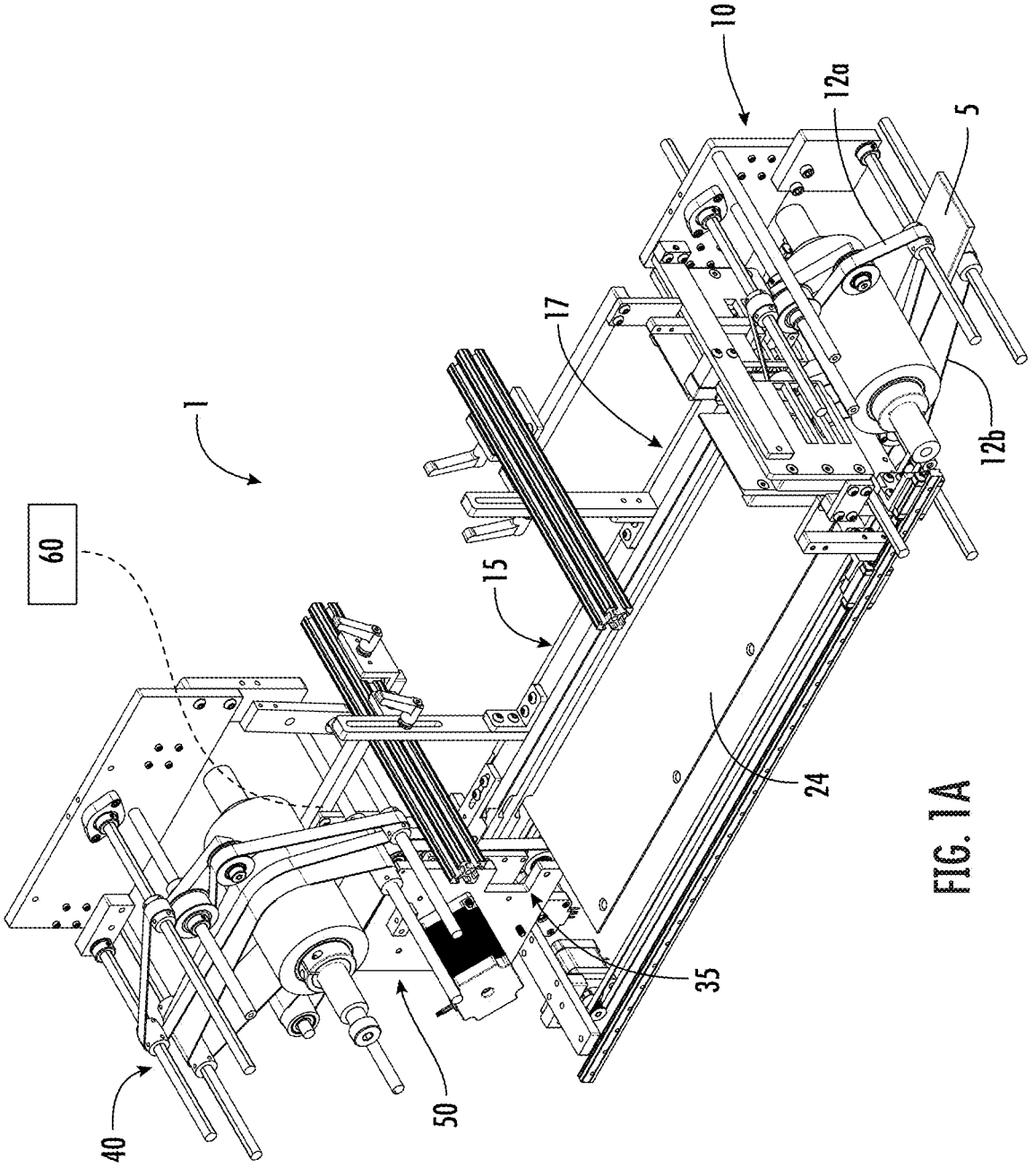
FIG. 1A is a top perspective view of a curing assembly.
Figure 1B:
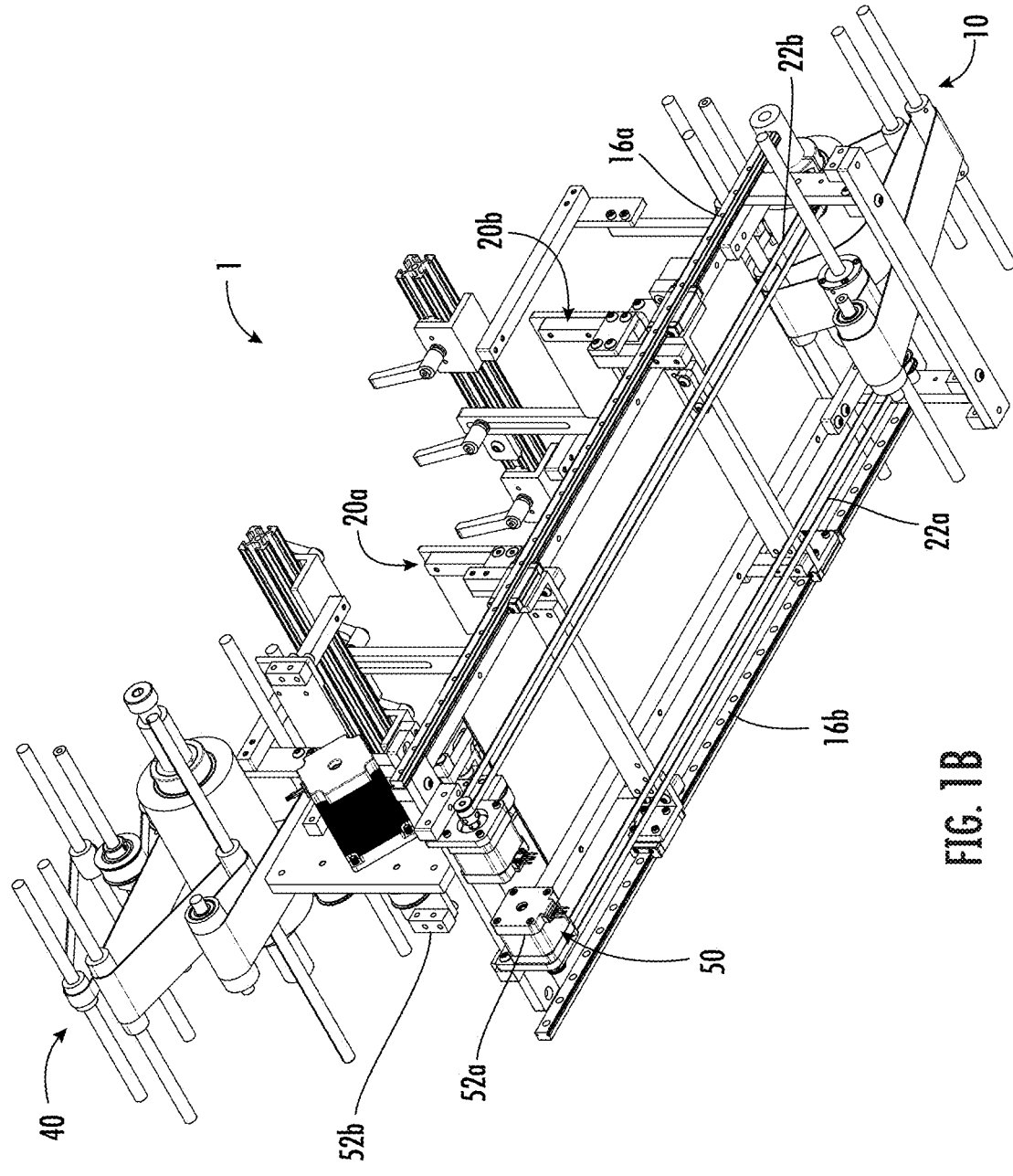
FIG. 1B is a bottom perspective view of the curing assembly.
Figure 1E:
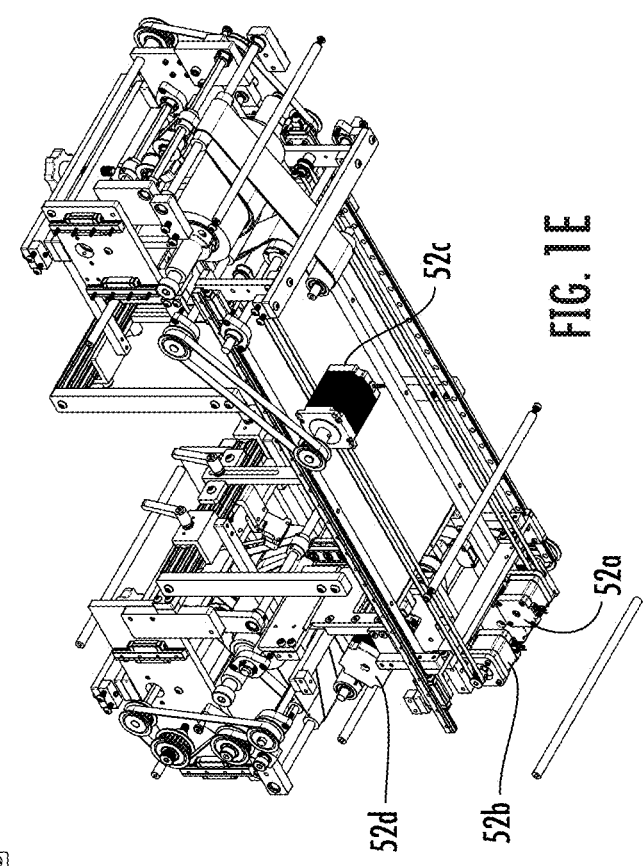
FIG. 1E is a bottom perspective view of the curing assembly.
Figure 1D:
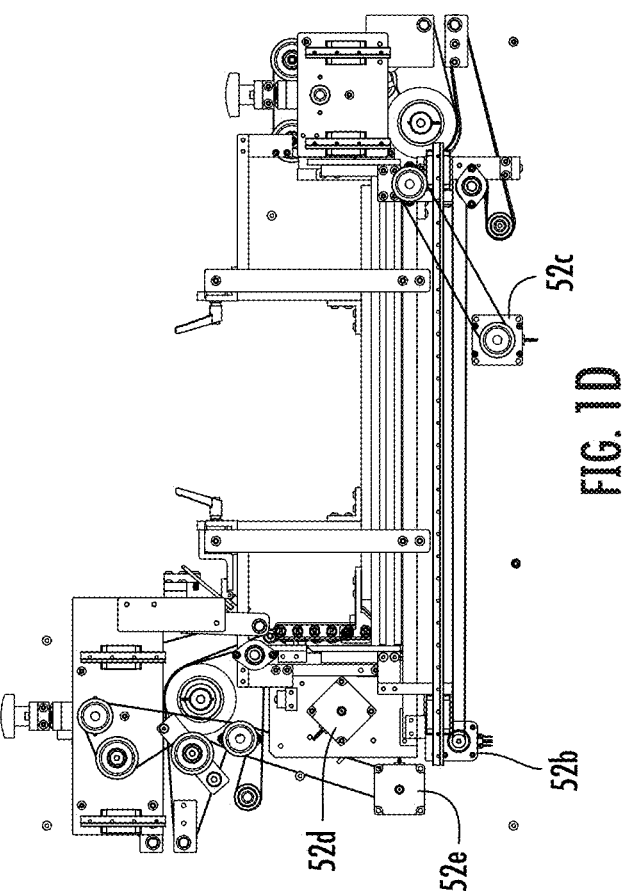
FIG. 1D is a side view of the curing assembly.

Certain terminology is used in the following description for convenience only and is not limiting. A reference to a list of items that are cited as "at least one of a, b, or c" (where a, b, and c represent the items being listed) means any single one of the items a, b, or c, or combinations thereof. The terminology includes the words specifically noted above, derivatives thereof and words of similar import.

As shown in FIGS. 1A-3, and 6A-9C, a curing assembly 1 is disclosed herein that is configured to receive products 5 and hold the products 5 in a stacked configuration (i.e. product stack) for a predetermined period. In one example, the products 5 can be arranged in a product stack with a leading edge and a trailing edge that are both engaged against a stop or support, such as a pressure plate or a belt.

The curing assembly 1 generally includes a track assembly 16, a first pressure plate assembly 20a attached to the track assembly 16, a second pressure plate assembly 20b attached to the track assembly 16, and a control assembly 50 configured to selectively drive the first pressure plate assembly 20a and the second pressure plate assembly 20b along the track assembly 16.

An input assembly 10 can be provided that is generally configured to feed products 5 to the curing assembly 1. The input assembly 10 can include at least one input belt, such as a first input belt 12a and a second input belt 12b. The first and second input belts 12a, 12b can be configured to engage a top and bottom surface of the products 5 as the products are driven towards the curing assembly 1. In one example, the input assembly 10 can be considered a stacking assembly because it drives the products 5 towards the curing assembly 1 such that the products 5 are driven into a stacked configuration (i.e. on-edge stacking). The first input belt 12a can be configured to engage a trailing edge of the product stack in one operating condition, such as the accumulating state, which is shown in FIG. 9C.

The first and second pressure plate assemblies 20a, 20b can have a similar or identical configuration as each other. In one example, the first pressure plate assembly 20a is a front pressure plate assembly and the second pressure plate assembly 20b is a rear pressure plate assembly.

Figure 4B:
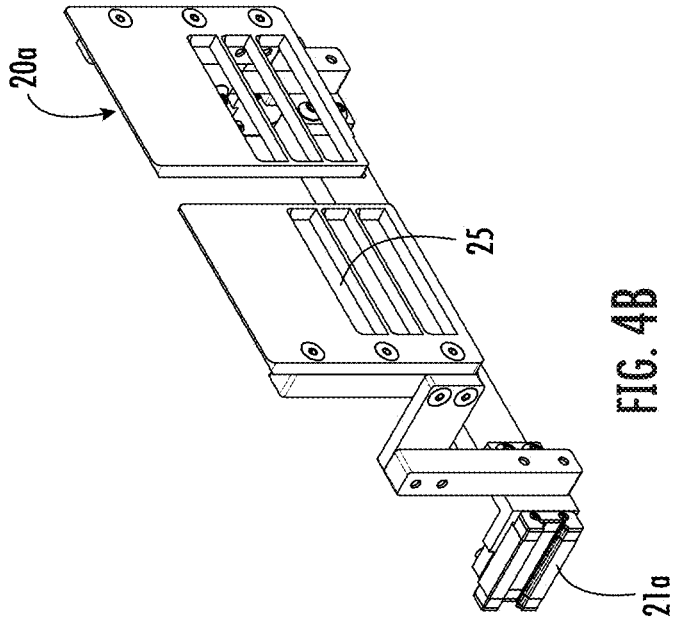
FIG. 4B is a perspective view of the first press plate assembly.
Figure 4A:
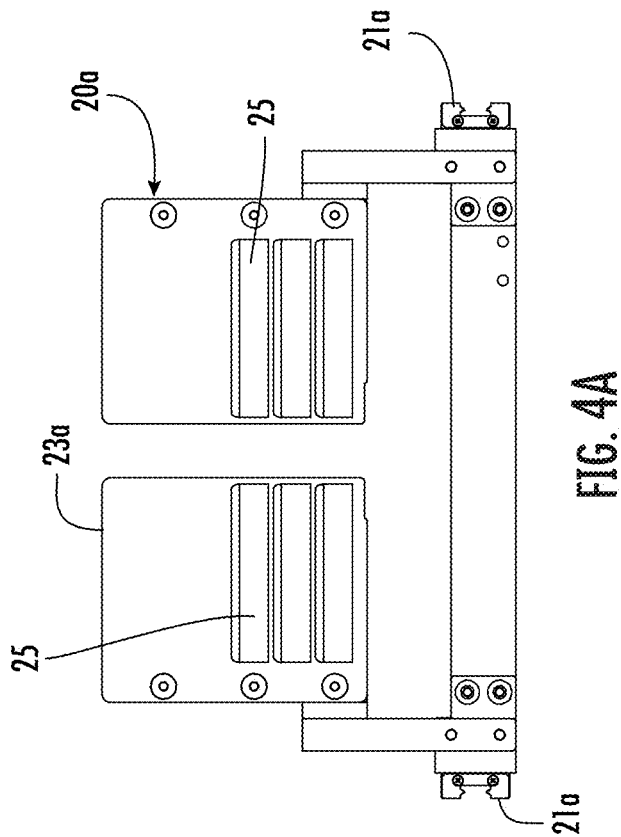
FIG. 4A is a front view of a first pressure plate assembly.

As shown in more detail in FIGS. 4A and 4B, the first pressure plate assembly 20a can include a first plate 23a and a first pressure plate carriage 21a. The first plate 23a can include a single plate with a gap or spacing in a medial region or can be formed as two separate plates that are connected with a gap therebetween. The gap or spacing can be configured to provide clearance or spacing for other components, such as a top guide, or belt assembly. The first pressure plate carriage 21a can include a slot configured to receive of a portion of the track assembly 16. Specifically, the first pressure plate carriage 21a can be configured to attach to a first and second track 16a, 16b of the track assembly 16. One of ordinary skill in the art would understand that the exact shape or profile of the first pressure plate assembly 20a can vary. Additionally, the second pressure plate assembly 20b can have the same features as the first pressure plate assembly 20a, such as a second pressure plate carriage 21b and a second plate 23b.

The first pressure plate assembly 20a and the second pressure plate assembly 20b can each include a plate 23a, 23b arranged in a parallel direction relative to the product stack. One of ordinary skill in the art would understand that the relative positioning of the first pressure plate assembly 20a and the second pressure plate assembly 20b, and the plates 23a, 23b can vary.

Figure 5:
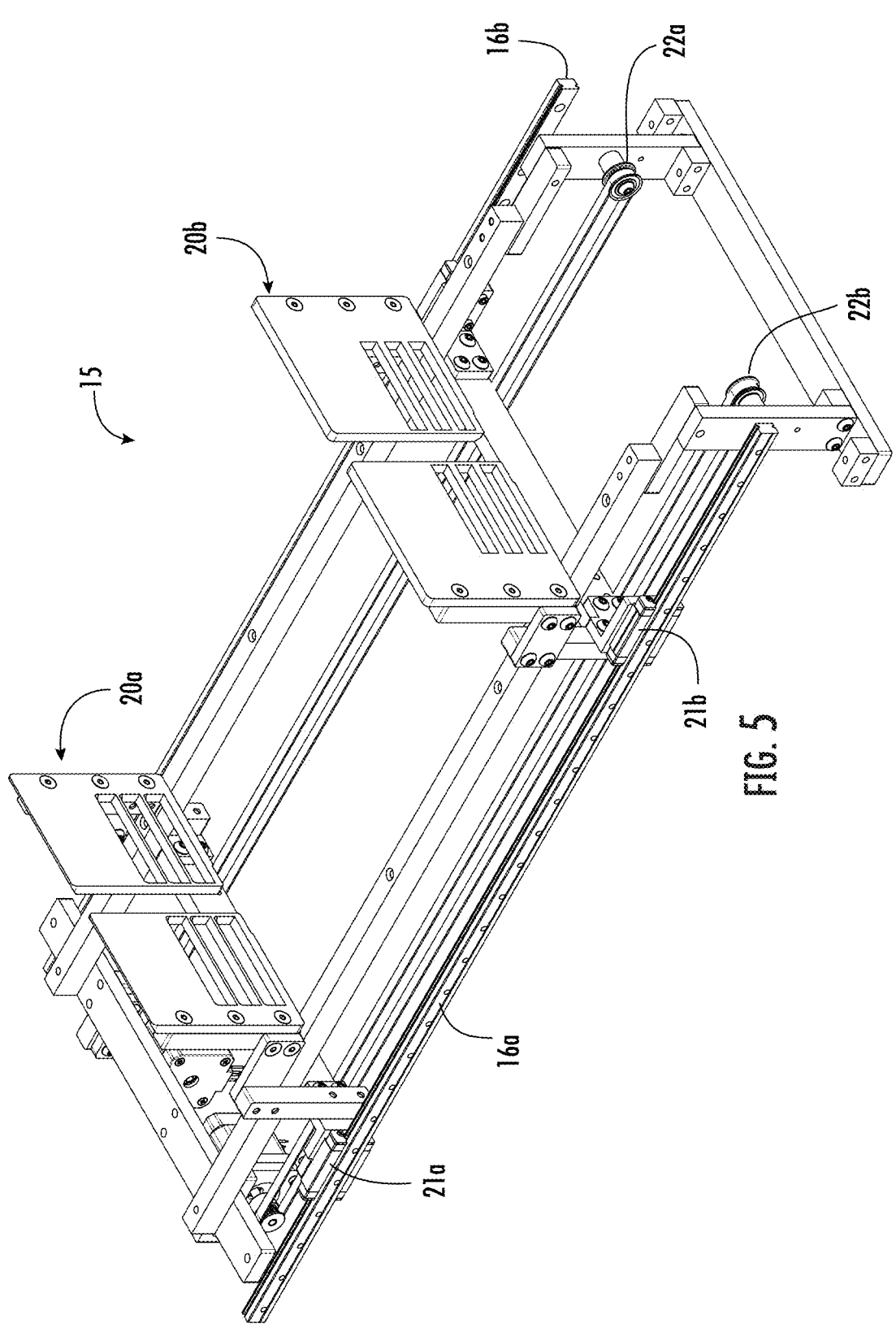
FIG. 5 is a perspective view of a rail assembly and first and second pressure plate assemblies.
Figure 6A:
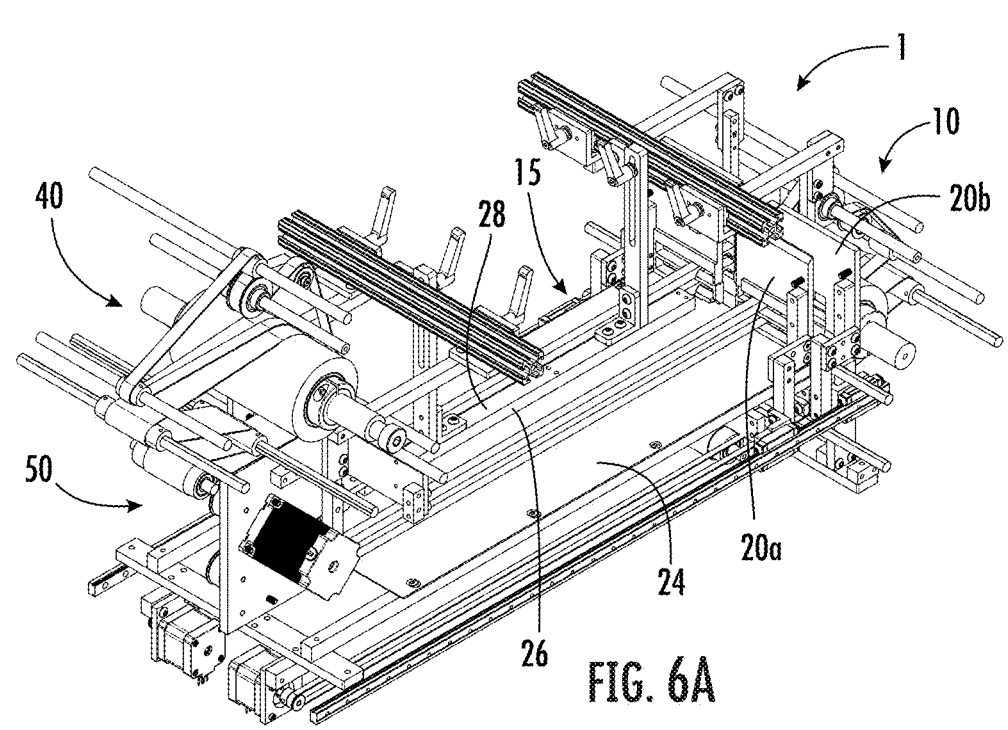
FIG. 6A is a first perspective view of the curing assembly during an initial state.
Figure 6B:
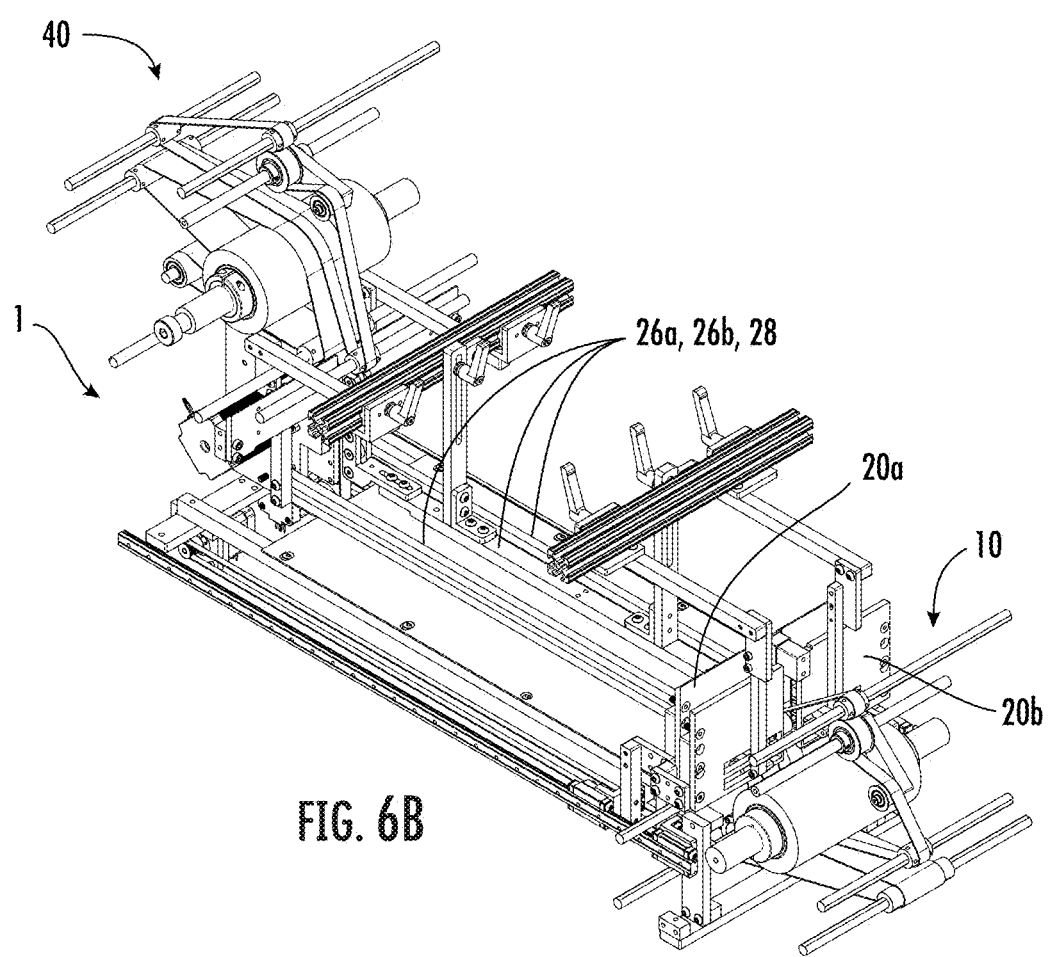
FIG. 6B is a second perspective view of the curing assembly during the initial state.

Movement of the first and second pressure plate assemblies 20a, 20b can be controlled via the control assembly 50. As used herein, the term control assembly 50 can refer to timing belts, motors, control units or controllers, and various other components. As shown in FIG. 5, a first pressure plate timing belt 22a can be provided for driving the first pressure plate assembly 20a, and a second pressure plate timing belt 22b can be provided for driving second pressure plate assembly 20b. The first pressure plate timing belt 22a and the second pressure plate timing belt 22b can be independently driven and controlled.

Figure 10A:
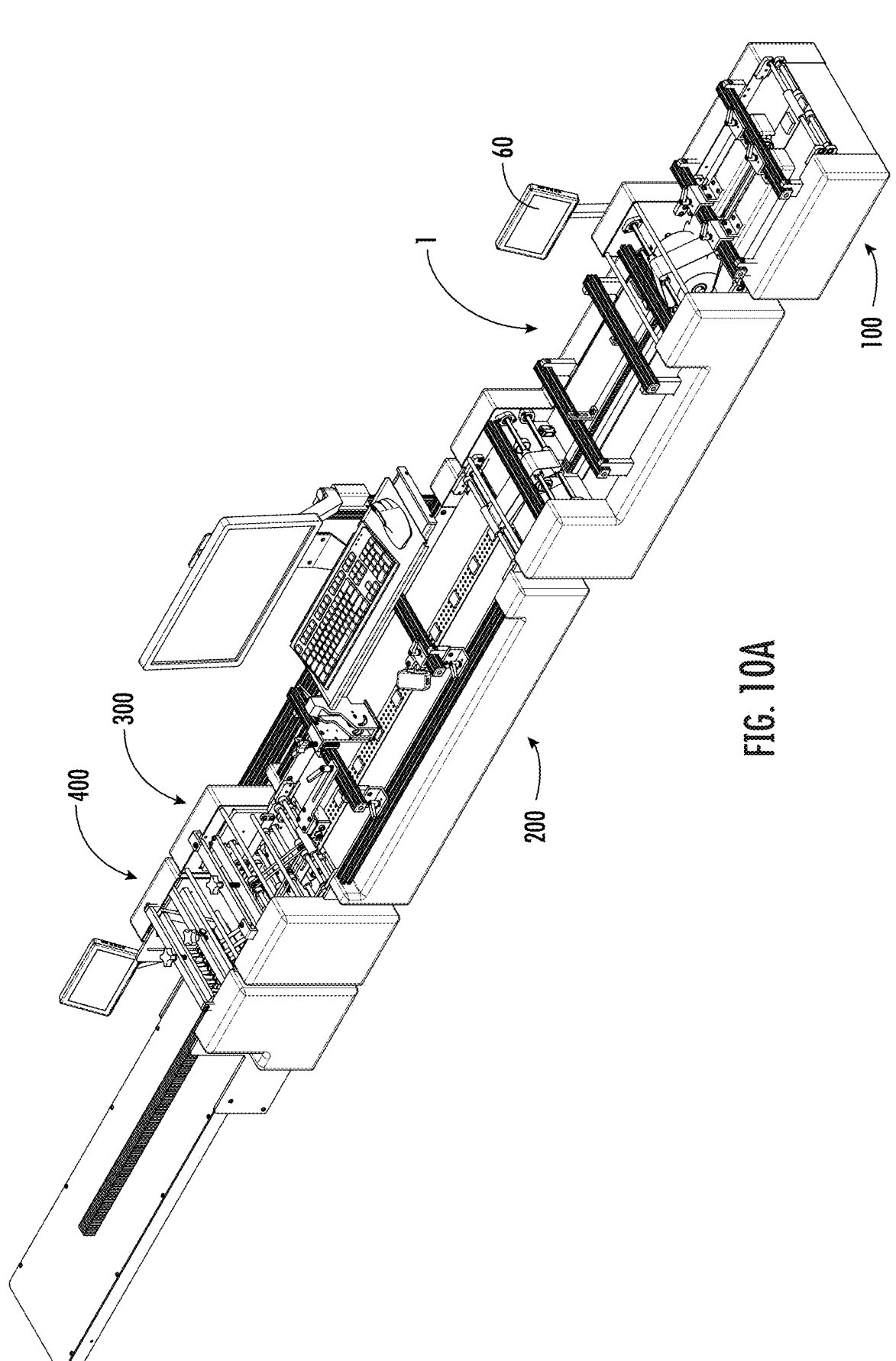
FIG. 10A is a perspective view of a complete arrangement including the curing assembly, among other assemblies.
Figure 12:
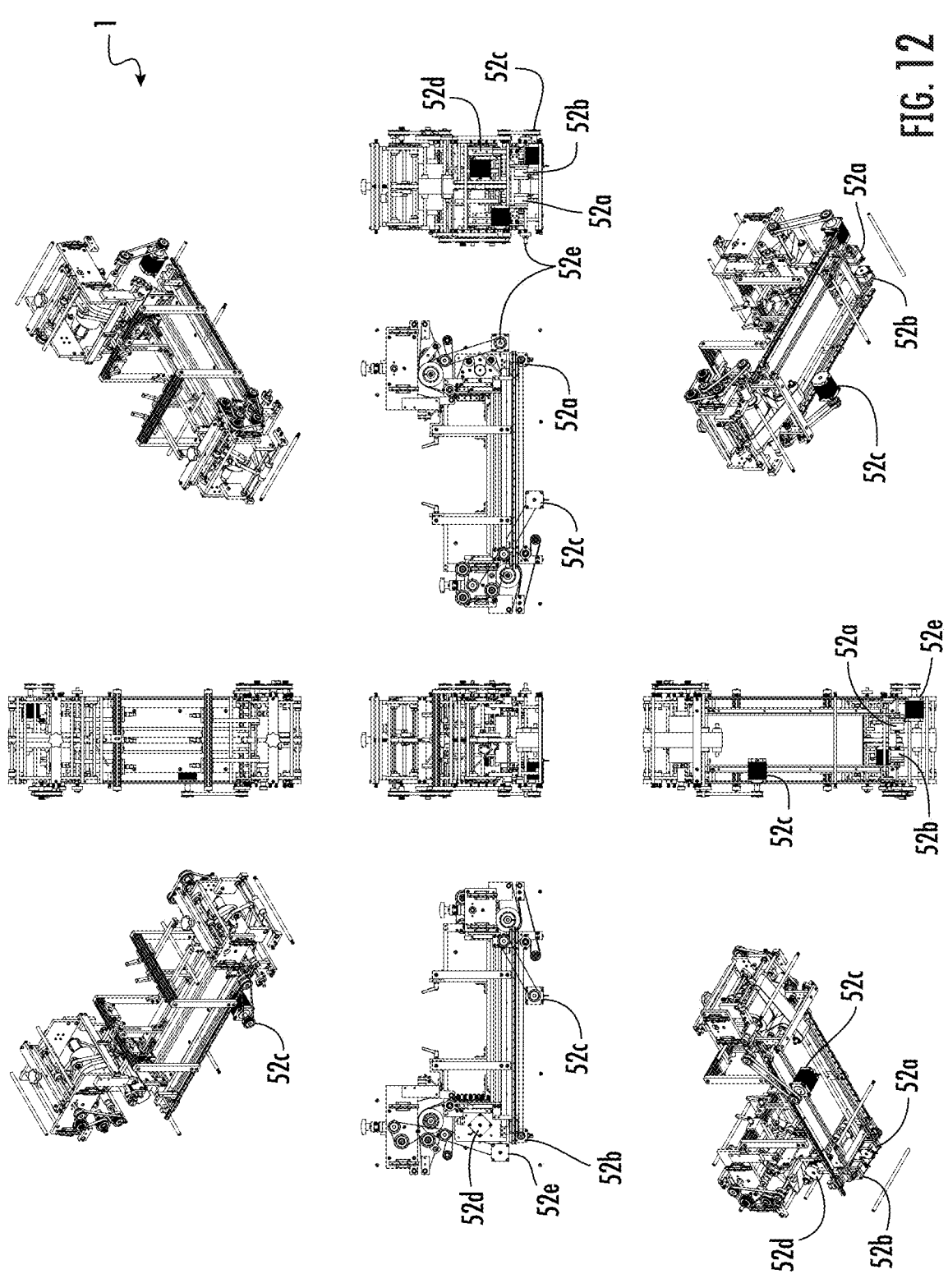
FIG. 12 illustrates a collection of views specifically showing motors for the curing assembly.

The control assembly 50 can include a control unit or controller configured to receive an input signal (such as via a manual input device, e.g., touchscreen, keyboard, etc.). The control assembly 50 can include a memory unit that is configured to store parameters associated with a wide range of products, such that the parameters can be automatically saved and loaded by users. As shown in FIG. 10A, a screen or monitor 60 can be provided that is configured to receive input from a user. The monitor 60 is also shown schematically in FIG. 1A. The monitor 60 can also include various information regarding the operation of the control assembly 50. The user can adjust multiple aspects of the system using the control assembly 50 and the monitor 60. Various input signals or settings can be adjusted to drive or control a motor. For example, parameters can be adjusted for controlling any one or more of the motors. FIG. 12 shows a collection of views of various exemplary motors for the curing assembly. As shown in more detail in FIGS. 1D and 1E, at least five motors 52a-52e can be provided. A first motor 52a (i.e. front pressure plate/wall motor) can be used to drive the first pressure plate assembly 20a. A second motor 52b (i.e. back pressure plate/wall motor) can be used to drive the second pressure plate assembly 20b. A third motor 52c (i.e. input motor) can be provided that is configured to drive the first and second input belts 12a, 12b. A fourth motor 52d (i.e. a discharge motor) can be provided for driving a singulator belt 36a. A fifth motor 52e (i.e. output motor) can be provided to drive first and second output belts 42a, 42b. The system can include modifying the parameters of the speed of each of these motors to adjust the motor's torque, duty cycle, speed, timing, etc. For example, when pushing products into the curing assembly 1, the first plate assembly 20a is creating pressure on the product stack. The accumulating products can push the first plate assembly 20a, and controlling the motors helps control exactly how far the first plate assembly 20a is driven based on the accumulating products. The control assembly 50 allows for specific adjustments of the motors, and other components, particularly due to varying conditions, such as the size, weight, etc. of the products, and other factors. The control assembly 50 allows for dynamic controlling and regulation of the curing assembly 1.

In one example, the first plate assembly 20a can be configured to be driven, held, or idled according to various operating parameters. For example, the first plate assembly 20a can be controlled via the associated motor to be put in an idle mode while several products enter the curing assembly, and then put into a hold mode while additional products enter the curing assembly. The number of products that are added during either of these modes can vary, and depend on the thickness, rigidity, amount of air in the products, compressibility, etc. In one example, the front plate assembly 20a can be held in the idle mode for five products, and then the hold mode for one product, and alternate between these modes accordingly. The pressure from the accumulating product stack can be configured to override the holding power of the motor associated with the front plate assembly 20, in one example.

One of ordinary skill in the art would understand that if the curing assembly is mounted in a vertical direction or an angled direction relative to a horizontal ground support surface, then a variable holding mode can be used instead of an idle mode, which would be undesirable due to gravitational forces on the components.

A rail assembly 15 can also be included that generally includes various supports or structures for supporting any of the elements or components described herein. A platform 24 can be provided that is attached to the rail assembly 15 or another support and can be configured to define a bottom support surface for the products 5.

The first pressure plate assembly 20a can be configured to apply a first predetermined pressure to a leading edge of the product stack at least during an initial stage of an accumulating state. The control assembly 50 can use a first motor 52a and the associated first pressure plate timing belt 22a to apply pressure to the product stack. Incoming products to the product stack can subsequently drive the first pressure plate assembly 20a forwards (i.e. to the left in FIG. 3) as the product stack grows.

The second pressure plate assembly 20b can be configured to apply a second predetermined pressure to a trailing edge of the product stack at least during final stage of an output state. The control assembly 50 can use a second motor 52b and the associated second pressure plate timing belt 22b to apply a similar force or pressure to the trailing edge of the product stack as was present when the products were being actively fed via the input assembly 10. In this way, the second pressure plate assembly 20b maintains the product stack in a compressed state as the leading edge of the product stack engages a discharge assembly 35 to drive the products downstream for further processing and inspection.

Figure 2:
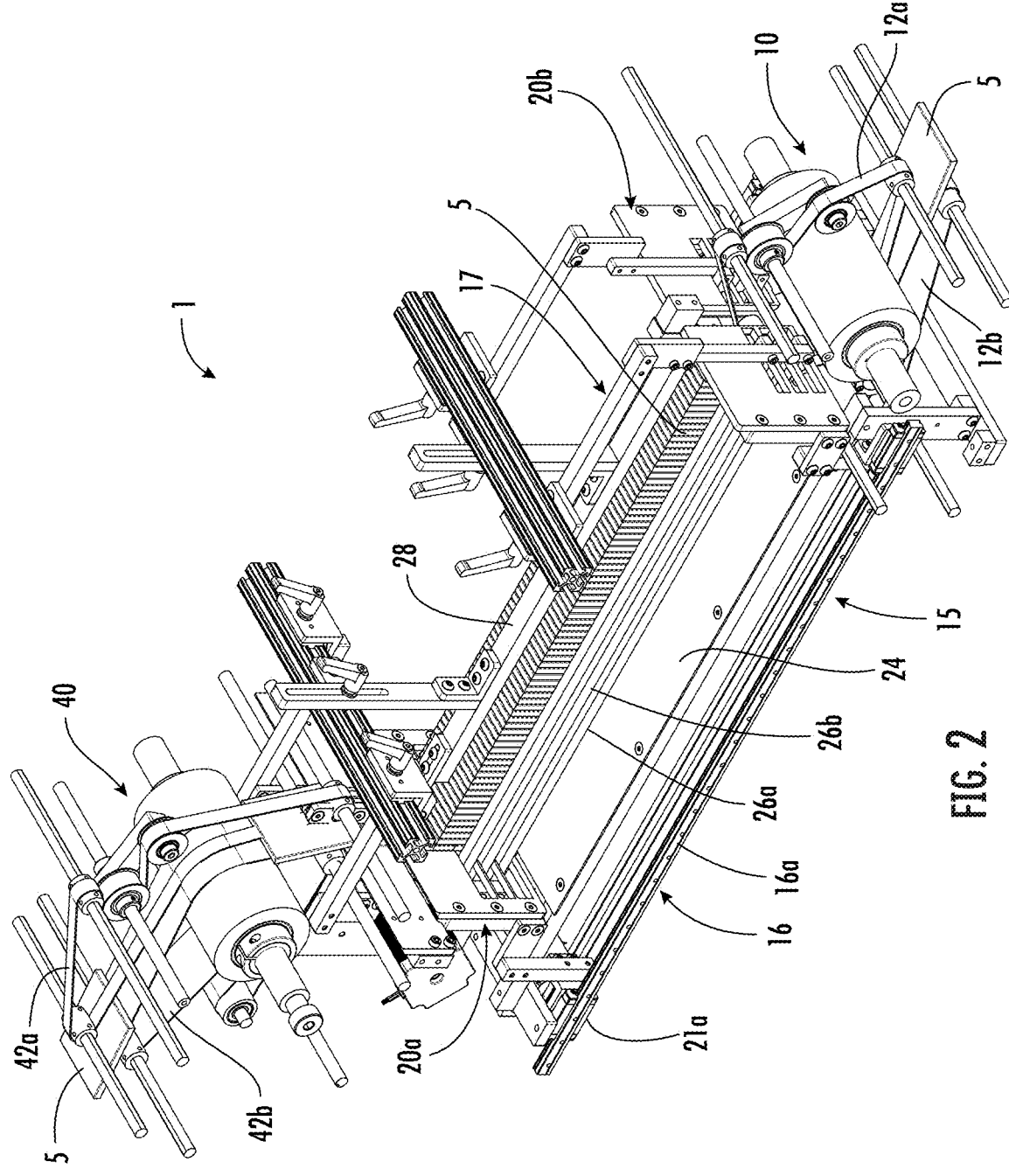
FIG. 2 is a perspective view of the curing assembly during a use state.
Figure 3:
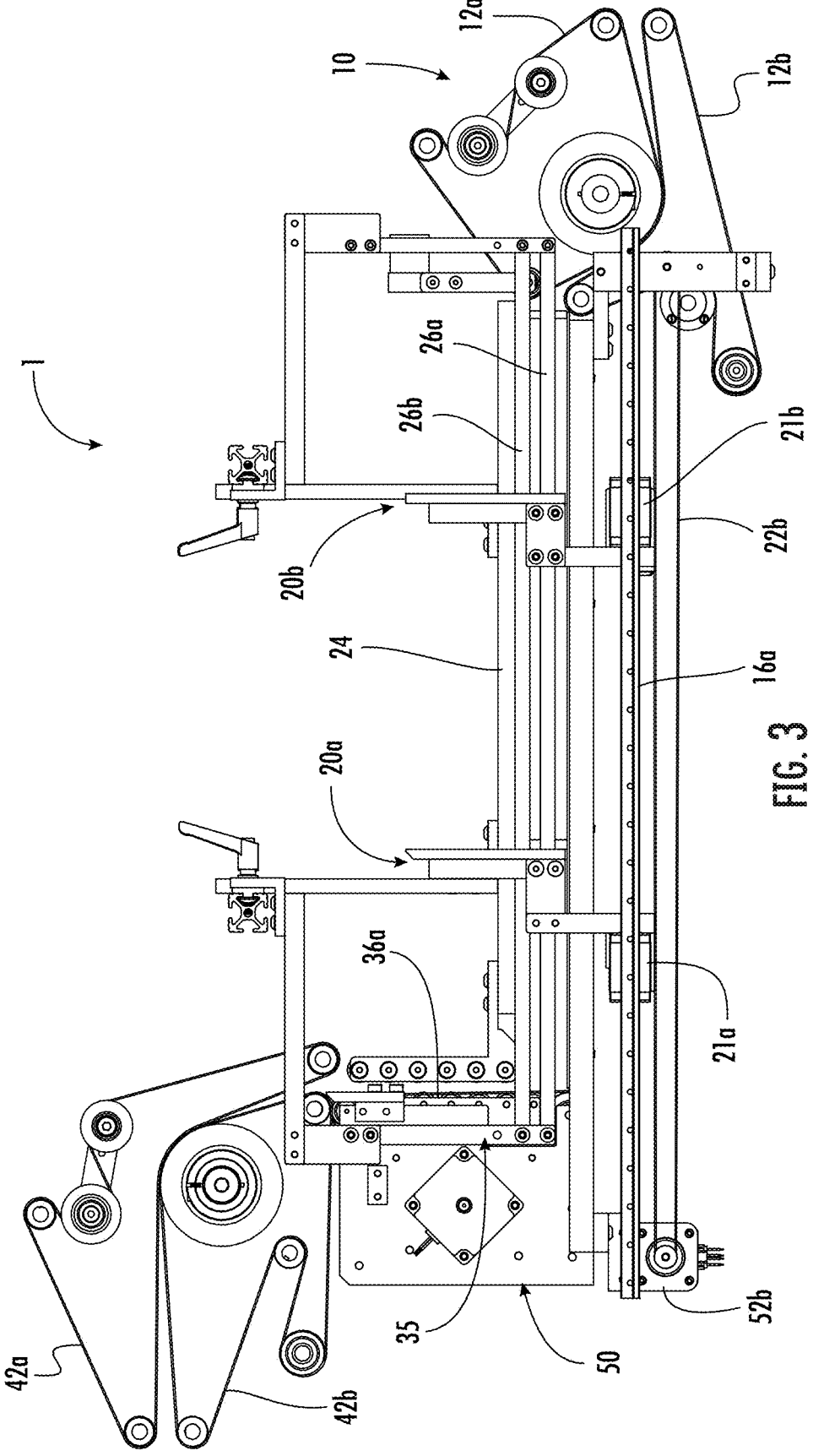
FIG. 3 is a side view of the curing assembly.

In one configuration, the accumulating state and the output state can occur at the same time. For example, as additional products 5 are fed into the curing assembly 1 via the input assembly 10, the products 5 already in the product stack can continuously be output from the curing assembly 1 via the discharge assembly 35. This condition is shown in FIG. 2, which shows products entering and leaving the curing assembly 1 at the same time.

In one example, the discharge assembly 35 is generally configured to drive products at the leading edge of the product stack away from the curing assembly 1. The discharge assembly 35 can be considered a singulator since it removes the leading product from the product stack and drives the product downstream for further processing. The discharge assembly 35 is shown in more detail in FIG. 9B. The discharge assembly 35 can include at least one discharge belt, such as singulator belt 36a. A singulator support 36b (i.e. rollers) can also be provided to engage an opposing surface of the products 5 relative to the singulator belt 36a. The position of the singulator support 36b can be adjustable. The singulator support 36b can include a plurality of rollers mounted to a frame or support component. The singulator belt 36a can be configured to drive the products 5 away from the product stack within the curing assembly.

In one configuration, the output state begins when the first pressure plate assembly 20a is driven out of contact with the product stack and the at least one singulator belt 36a begins engaging the leading edge of the product stack to drive the products upward and away from the curing assembly 1.

Figure 10B:
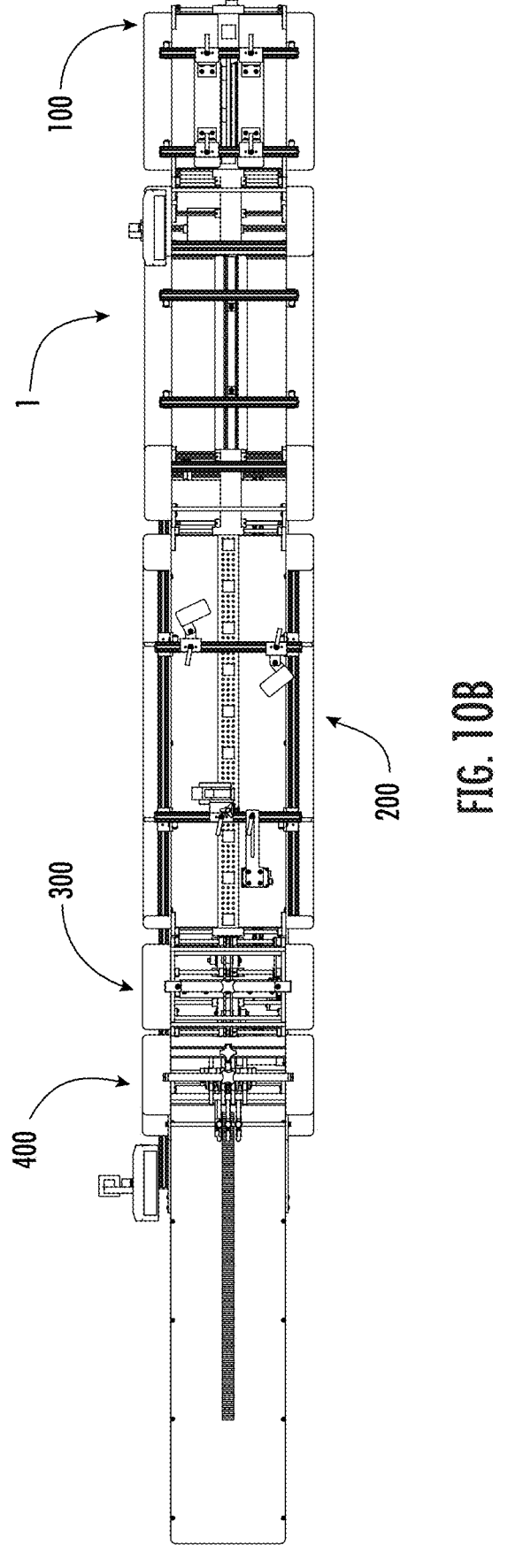
FIG. 10B is a top view of the complete arrangement of FIG. 10A.

An output assembly 40 can be arranged adjacent (i.e. downstream) to the discharge assembly 35. The output assembly 40 can include a first output belt 42a and a second output belt 42b. In one example, the first and second output belts 42a, 42b can be configured to engage an upper and lower surface of the products 5 as the products 5 are discharged from the curing assembly 1 via the discharge assembly 35. In one configuration, a speed of the first and second output belts 42a, 42b is greater than a speed of the singulator belt 36a. One of ordinary skill in the art would understand that other configurations for an output assembly can be used. For example, the output assembly 40 may only require one belt that is configured to engage a bottom surface of the products 5 and advance the products 5 downstream. The output assembly 40 can generally be configured to direct the now-cured products towards an inspection area (i.e. inspection system 200 as shown in FIGS. 10A and 10B).

The first pressure plate assembly 20*a* can be driven by the control assembly 50 out of contact with the product stack during the output state. This allows the products on the leading edge of the product stack to engage with the discharge assembly 35, and specifically engage against the running singulator belt 36*a* such that the products 5 are individually separated from the product stack.

Figure 7:
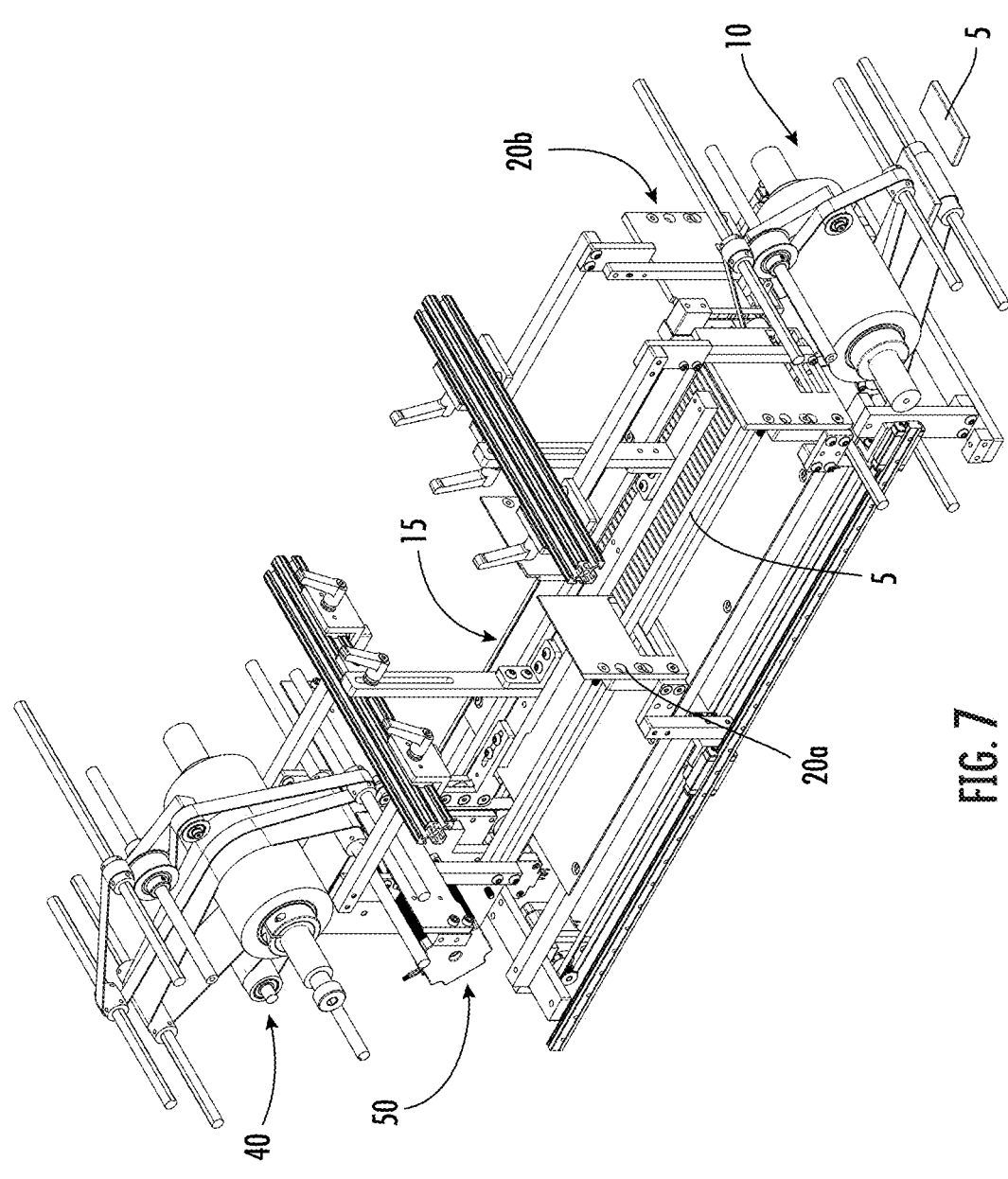
FIG. 7 is a perspective view of the curing assembly during an accumulating state.
Figure 8A:
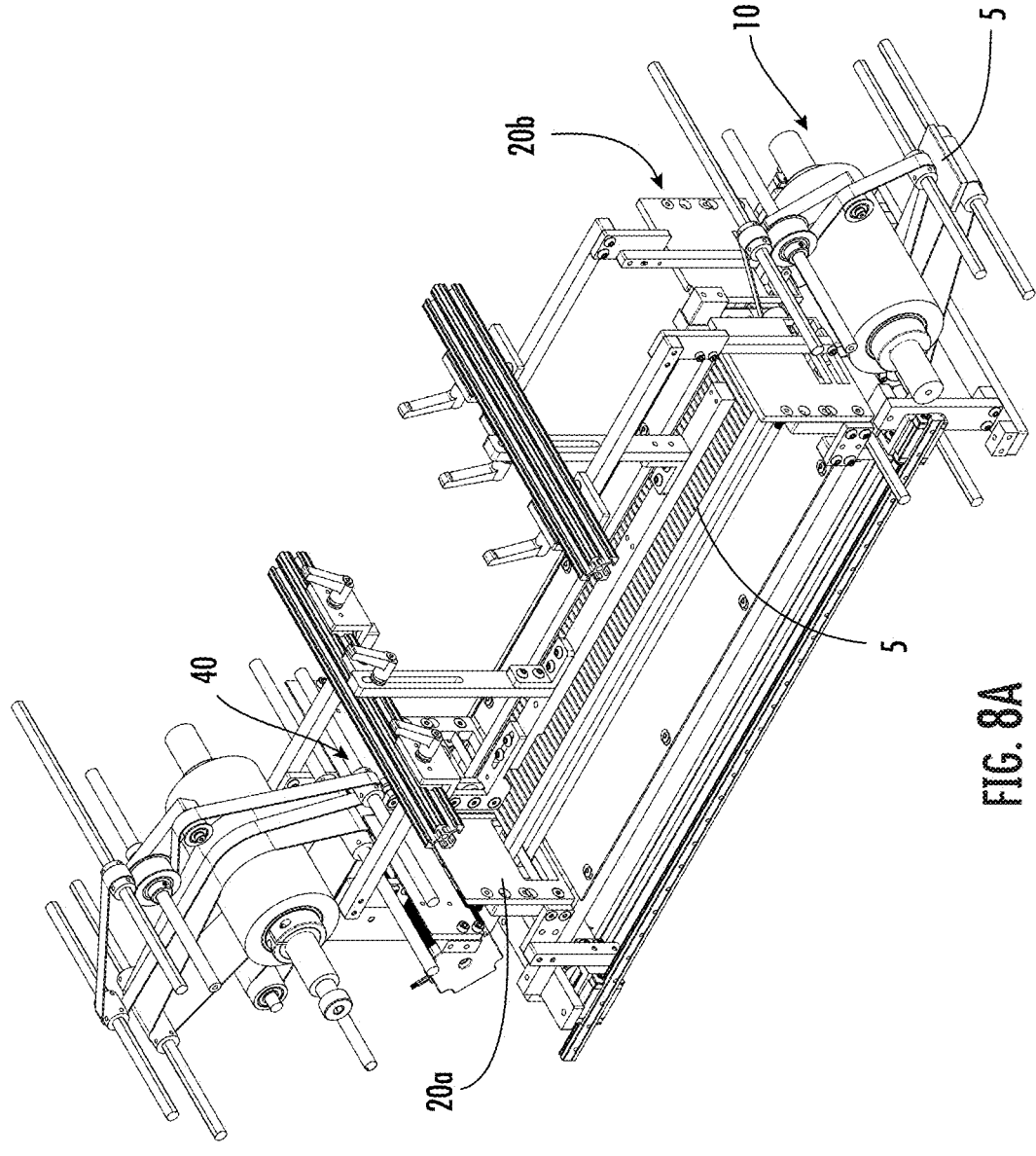
FIG. 8A is a perspective view of the curing assembly during the accumulating state and immediately before an output state.
Figure 8B:
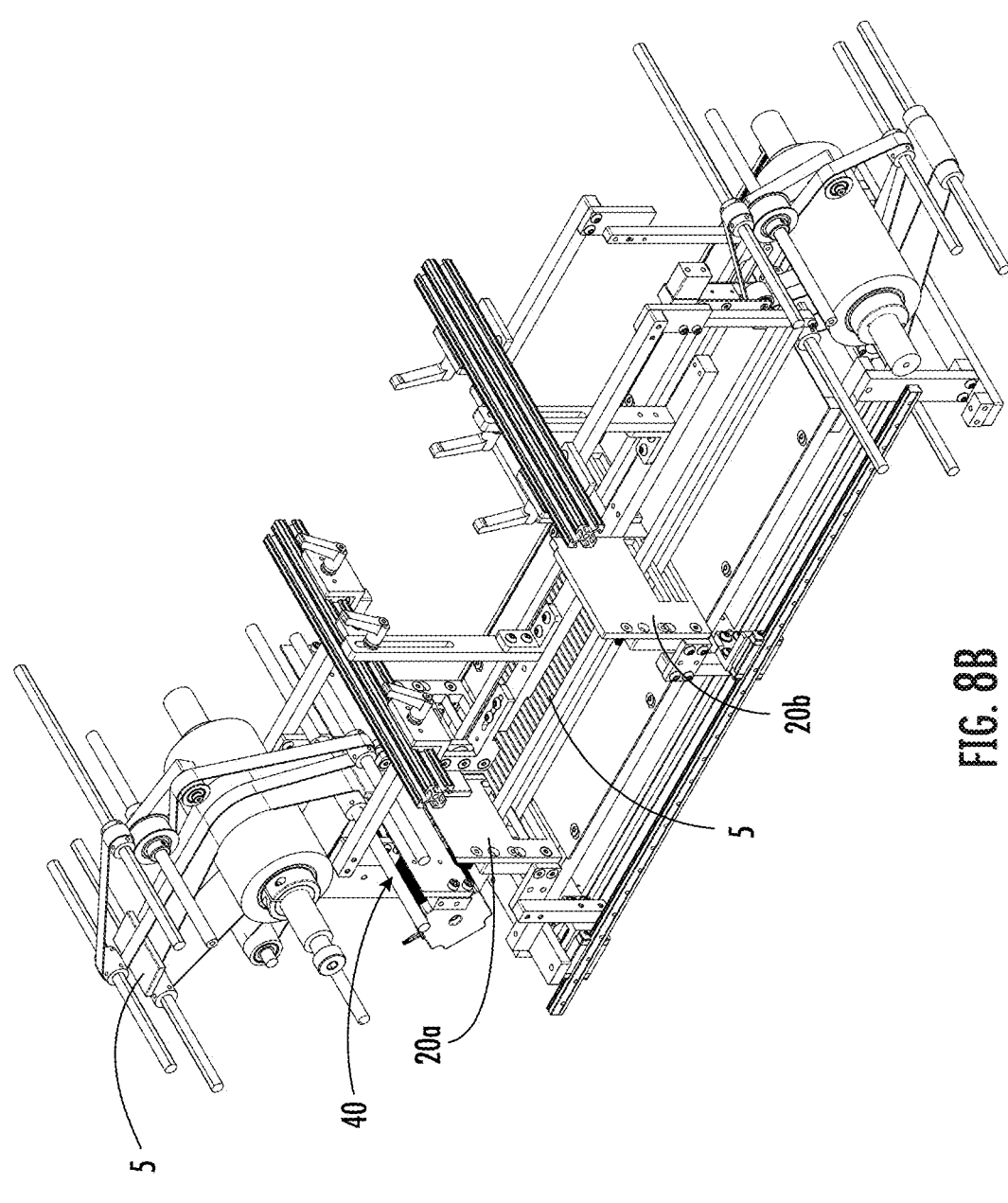
FIG. 8B is a perspective view of the curing assembly during an end of an output state.

The second pressure plate assembly 20*b* can be positioned away from the product stack during the accumulating state. This configuration allows the input assembly 10 to continuously drive products 5 into the product stack during the accumulating state. FIG. 7 illustrates one aspect of the accumulating state, which shows the curing assembly 1 half-full with products 5. FIG. 8A shows another aspect of the accumulating state, which shows the curing assembly 1 almost completely full of products 5 (i.e. just prior to the products 5 being discharged). FIG. 8B shows an aspect of the output state, as the product stack is shown half full. In FIG. 8B, the products 5 are being separated from the product stack and fed or singulated to the output assembly. The second pressure plate assembly 20*b* is pushing the back end of the product stack to ensure pressure is maintained.

An overhead guide assembly 17 can be provided that is configured to engage an upper portion of the products 5 as the products 5 are driven into the product stack via the input assembly 10. The overhead guide assembly 17 can include an overhead guide 28, which can a rail, bar, plate, or other structure. This is shown in more detail in FIG. 9C. In one example, a height of the overhead guide assembly 17 is adjustable. Adjusters, such as manual handles, release mechanisms, levers, etc., can be included with the overhead guide assembly 17 to adjust the height of the overhead guide 28. If too high of a pressure is applied to the product stack, then the products tend to be driven upward. The overhead guide assembly 17 provides an abutment surface to prevent the product stack from bowing upward as pressure is applied to the product stack.

In order to laterally guide the product stack, a side guide assembly 26 can be provided. The side guide assembly 26 can include a plurality of side guide rails 26*a*, 26*b*, 26*a'*, 26*b'*. The side guide rails 26*a*, 26*b*, 26*a'*, 26*b'* can be configured to be partially received within slots or openings 25 of the plates 23*a*, 23*b* of the plate guide assemblies 20*a*, 20*b*. One of ordinary skill in the art would understand that the exact configuration of the side guide assembly 26 can vary. A width of the side guide assembly 26 can be adjustable. Adjusters, such as manual handles, release mechanisms, levers, etc., can be included with the side guide assembly 26 to adjust the lateral positioning of the plurality of side guide rails 26*a*, 26*b*, 26*a'*, 26*b'*. Side guide adjustment rails 27*a*, 27*b* can be provided that are connected to an adjustment assembly 29. The adjustment assembly 29 include various adjusters that can independently adjust positions of the side guide rails 26*a*, 26*b*, 26*a'*, 26*b'*, as well as the overhead guide 28. The side guide assembly 26 prevents the product stack from bowing or caving in either lateral direction due to high pressure being applied to the product stack.

The pressure that is applied to the product stack can vary, depending on the type of adhesive that is used, size of the product stack, ambient conditions, and other factors. In one configuration, the product stack includes a plurality of pamphlets, brochures, or other substrates that include layers of material that are partially adhered to each other, such as via a pressure-sensitive adhesive. In one configuration, the product stack consists of a plurality of pharmaceutical leaflets or outserts. One of ordinary skill in the art would understand that the type of product being handled by the curing assembly 1 can vary.

In one configuration, the accumulating state is at least 20 seconds. This period or cycle can vary depending on the size of the product stack, as well as the type of pressure-sensitive adhesive that may be applied to products within the product stack prior to entering the curing assembly.

In one configuration, only one of the first pressure plate assembly 20*a* and the second pressure plate assembly 20*b* is engaged with the product stack in both the accumulating state and the output state. This can vary depending on the specific process that the curing assembly is being used for. In one process, neither the first pressure plate assembly 20*a* nor the second pressure plate assembly 20*b* need to be engaged with the product stack. Instead, the product stack can be continuously cycled through the curing assembly 1, such that the leading edge of the product stack is engaging the singulator belt 36*a* as the trailing edge of the product stack is engaging the input belt 12*a*.

In one example, the curing assembly is configured to allow a user to input a desired number of products to be held within the product stack. This information can be entered via the control assembly 50, in one example. In one configuration, a user may enter a quantity of 100 products to be maintained within the stack held by the curing assembly. The curing assembly can operate on a first in, first out (FIFO) model in which as one product enters the stack, then another product leaves the stack. During operation, a user can manually inspect the product stack being held within the curing assembly. Users can engage a side of the product stack to determine how much pressure is being applied to the product stack. If the product stack is relatively firm, then the user can determine that the adequate pressure is being applied and the pressure sensitive adhesive will likely dry. In the event that the product stack is loose, then the user may determine that a great pressure must be applied to ensure drying of the adhesive. Accordingly, a user can change the parameters such that instead of X products being held in the product stack, now X+10 products will eb held within the product stack.

Regarding timing of the motors and belts, one of ordinary skill in the art would understand that various parameters can be set based on a number of different factors. For example, if the processing assembly upstream of the curing assembly is running at X speed, then a linearization model can determine the speed necessary for the input assembly to be running, i.e. Y speed. Various correlation models and configurations can be used to ensure that the curing assembly is keeping up with the number of products being input.

Once a batch of products are handled by the curing assembly 1, both the first pressure plate assembly 20*a* and the second pressure plate assembly 20*b* can be driven or controlled to move to a position out of the flow path for products.

Various modes and states can be implemented for the curing assembly. The output state or mode can also vary, and can include (i) an emptying-output state in which products are no longer being fed to the curing assembly and products are only being discharged, and (ii) a combined input-output state in which products are continuously fed and discharged from the curing assembly. For example, one mode can include an "Empty" command or "Empty Curing" command in which both of the first and second plate assemblies are engaged with a product stack, or in which only the second plate assembly is engaged with the product stack. When a user wishes to empty the curing assembly, perhaps due to a malfunction or deformation associated with the product stack, then the user can press a button on the monitor and the curing assembly will drive the second plate assembly forward, thus moving the products and the first plate assembly towards the discharge assembly 35 and singulator.

One of ordinary skill in the art would understand that engaging the monitor 60 to empty the curing assembly automatically stops any upstream feeding of products to the curing assembly because the plates are not in the accumulating positions.

In one example, the monitor 60 has a power up button and a start button. When these buttons are engaged, the plate assemblies will be driven to a home position (i.e. a position in which the plates are positioned to begin accepting products from the input). The first plate assembly can be driven in a direction generally towards the input assembly, and the first plate assembly may engage with the second plate assembly if the second plate assembly is not already in its home position. If any lingering products are still in the curing assembly, then a sensor is configured to detect these products during this start up phase and can alert a user to remove the old products.

Referring to FIGS. 10A and 10B, upstream and downstream assemblies relative to the curing assembly 1 are illustrated. More specifically, a registration/forming system 100 can be provided upstream from the curing assembly 1. The registration/forming system 100 can generally be configured to receive products from a folder. The registration/forming system 100 can be configured to register and square the products coming from the folder before entering the curing assembly 1. In one arrangement, the registration/forming system 100 can include guide elements that engage inwardly relative to the products to ensure that the edges of the products are aligned.

An inspection system 200 can be provided downstream from the curing assembly 1. The inspection system 200 can be configured to identify unglued products, i.e. inserts/outserts. The inspection system 200 can be configured to inspect each product to make sure that each product is visually and dimensionally to a specific customer's specifications. The inspection system 200 can include various cameras or other visual inspection elements that are configured to detect any defects in the products. Based on the curing assembly 1 and its arrangement, the inspection system 200 can perform its visual inspection process without requiring belts to apply pressure on two sides of the products 5 exiting the curing assembly 1. In the current state of the art, inspection systems sometimes require continuous pressure to two sides (i.e. top and bottom) of the products. In contrast, the inspection system 200 allows for a user to examine whether a product is fully glued and dried without the requirement of maintaining pressure via a top and bottom belt. This ensures a more complete analysis of the products.

A divert system 300 can be provided downstream from the inspection system 200. The divert system 300 can generally be configured to automatically reject or divert any products that are flagged by the inspection system 200.

A stacker assembly 400 can be provided downstream from the divert system 300. The stacker assembly 400 can be configured to stack the acceptable products onto a platform at the end of the process. In one configuration, this stacking can be done in the vertical direction.

Figure 11:
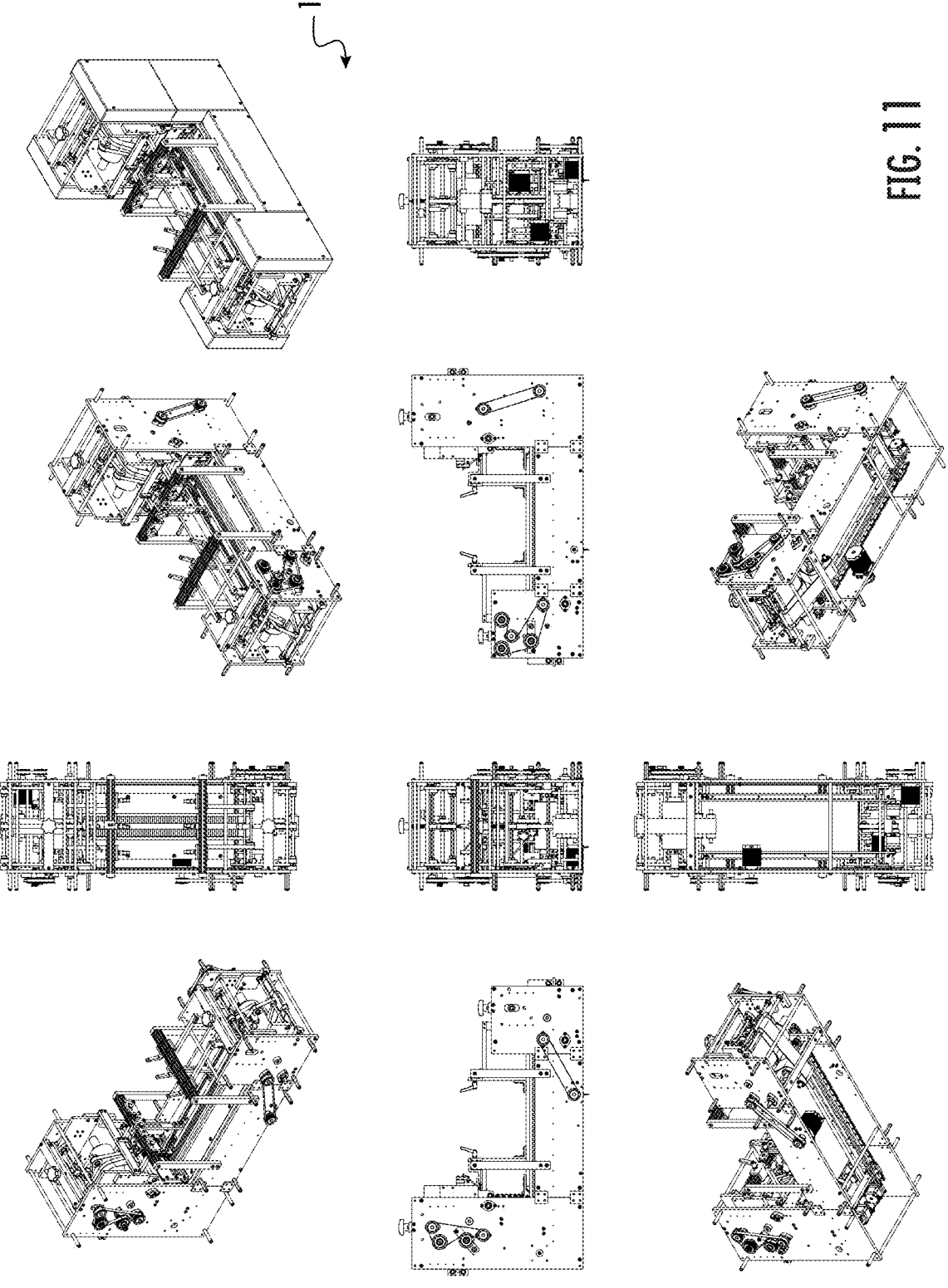
FIG. 11 illustrates a collection of views of the curing assembly with covers attached.

As shown in FIG. 11, various covers can also be arranged on faces of the curing assembly.

A method of applying pressure to products for curing adhesive is also disclosed herein. The method can include feeding the products to a curing assembly to form a product stack. The method can then include engaging a leading edge of the product stack with a first pressure plate assembly at least during an initial stage of an accumulating state such that a first predetermined pressure is applied to the product stack. The method can also include engaging a trailing edge of the product stack with a second pressure plate assembly at least during a final stage of an output state such that a second predetermined pressure is applied to the product stack. Finally, the method can include discharging the products from the curing assembly.

The method can further include adjusting a pressure applied to the product stack via adding or removing products from the product stack held within the curing assembly, wherein the curing assembly defines a predetermined area for the product stack. The curing assembly can define a predetermined area between the output assembly and singulator, i.e. when the plate assemblies are not engaged with the product stack. This predetermined area is fixed, thereby allowing a user to adjust the amount of pressure applied to the product stack held within the curing assembly by adding or removing products from the product stack. The products are compressible due to air and other factors, and therefore the pressure can be adjusted by adding or removing products from the product stack. The method can also include applying a constant pressure to the product stack during a combined input-output state in which a constant number of products are fed and discharged to the curing assembly. During this combined state, products are both input to the curing assembly and output from the curing assembly. The method can further comprise driving the first pressure plate assembly forward via contact with an accumulating product stack. During this step, the motor driving the first pressure plate assembly can either be in an idle mode, or a limited torque mode such that the growing product stack can overcome the opposing force that would otherwise be applied via the first pressure plate assembly.

Any one or more of the steps mentioned above can be occurring simultaneously and overlap with any one or more of the other steps.

As explained above, a method and apparatus for storing folded and recently glued leaflets or booklets, such as pharmaceutical outserts, under pressure to allow glue or adhesive to completely cure prior to feeding each piece one at a time to a post-processor is disclosed. The apparatus can include a frame connected in-line with a folding system, an on-edge stacker for moving a stack of booklets, a front plate (i.e. first plate), for keeping the stack under pressure at the start of the process, a back plate (i.e. second plate) for keeping the stack under pressure at the end of the process. The output feeder can feed fully dry booklets one at a time while maintaining the exact number of booklets in the stacker which allows adhesive to dry for at least 20 second or more under pressure.

The present disclosure provides a relatively compact system that automatically accepts folded and glued booklets from a folding system for storing these booklets under pressure and feeding these booklets to the post-processor after each booklet is completely cured. In one embodiment, the system includes an input stacking mechanism for placing booklets onto a hopper of on edge stacker. The front pressure plate can keep stacked booklets on edge while providing pressure on the foremost booklet or product (i.e. trailing edge). The subsequent booklet or product entering the on-edge stacker pushes the entire stack of booklets and the front pressure plate towards the end of the stacker. Additionally, the present disclosure provides the feeder at the end of on-edge stacker so that booklets can be discharged after conditions of a required discharge are met (i.e. the adhesive is fully cured or dry). In addition, the feeder may include a singulator or separator assembly for separating individual booklets prior to delivering each booklet to the feeder.

The back pressure plate can move a stack of booklets towards the feeder section of the apparatus at the end of the process or when there are no more booklets delivered from the folding system. The back pressure plate is configured to duplicate the function of each incoming booklet from the folder system by continuously moving the entire stack of booklets toward the feeder section while providing a pressure of the last received booklet. The present disclosure provides side guide rails and an upper guide rail for making adjustment for the width and length of the incoming booklets while providing no interference to front pressure plate nor back pressure plate operation. The front pressure plate and back pressure plate are controlled by the precision motors that may maintain different type of pressure depending on the material and the type of fold of incoming booklets. Multiple sensors control the speed of incoming and outgoing booklets as well as controlling the precise position of the front and back pressure plates. For example, an input sensor can be provided in the area of the input assembly 10, a monitoring sensor can be arranged around the product stack to ensure the products are stacked on their edges, a position sensor can be arranged adjacent to each of the front and back plate assemblies to determine their positions, a sensor can be provided adjacent to the singulator, and another sensor can be arranged adjacent to the output assembly. One of ordinary skill in the art would understand that sensors could be implemented in any number of locations and positions relative to the curing assembly. The sensors can communicate with each other and other components of the system, such as the motors, to control the timing, speed, and other parameters of the curing assembly.

The present curing assembly provides advantages, particularly regarding control and precision, as compared to other systems that may rely on counterweights to apply pressure to the product stack. Counterweights have a fixed mass and therefore the pressure applied to the product stack is difficult to control without manually adjusting the weights. In comparison, the motors disclosed herein provide variable controls for the amount of pressure applied to a product stack.

Having thus described the present disclosure in detail, it is to be appreciated and will be apparent to those skilled in the art that many physical changes, only a few of which are exemplified in the detailed description of the invention, could be made without altering the inventive concepts and principles embodied therein.

It is also to be appreciated that numerous embodiments incorporating only part of the preferred embodiment are possible which do not alter, with respect to those parts, the inventive concepts and principles embodied therein.

The present embodiment and optional configurations are therefore to be considered in all respects as exemplary and/or illustrative and not restrictive, the scope of the embodiments being indicated by the appended claims rather than by the foregoing description, and all alternate embodiments and changes to this embodiment which come within the meaning and range of equivalency of said claims are therefore to be embraced therein.

What is claimed is:

1. A curing assembly comprising:
a track assembly;
an overhead guide assembly configured to engage an upper portion of the product stack, with a height of the overhead guide assembly being adjustable;
a first pressure plate assembly attached to the track assembly;
a second pressure plate assembly attached to the track assembly; and
a control assembly configured to selectively drive the first pressure plate assembly and the second pressure plate assembly along the track assembly;
wherein products are configured to be fed to the curing assembly such that the products are stacked against one another to form a product stack,
the first pressure plate assembly is configured to apply a first predetermined pressure to a leading edge of the product stack at least during an initial stage of an accumulating state; and
the second pressure plate assembly is configured to apply a second predetermined pressure to a trailing edge of the product stack at least during final stage of an output state.

2. The curing assembly according to claim 1, wherein the first pressure plate assembly is driven by the control assembly out of contact with the product stack during the output state.

3. The curing assembly according to claim 1, wherein the second pressure plate assembly is positioned away from the product stack during the accumulating state.

4. The curing assembly according to claim 1, further comprising a side guide assembly including at least one side guide rail configured to guide lateral portions of the product stack.

5. The curing assembly according to claim 4, wherein a width of the side guide assembly is adjustable.

6. The curing assembly according to claim 4, wherein the first and second pressure plate assemblies each include at least one opening configured to receive the at least one side guide rail.

7. The curing assembly according to claim 1, further comprising a discharge assembly including at least one discharge belt, wherein the at least one discharge belt is configured to engage the leading edge of the product stack during the output state.

8. The curing assembly according to claim 7, wherein the output state begins when the first pressure plate assembly is driven out of contact with the product stack and the at least one discharge belt begins engaging the leading edge of the product stack.

9. The curing assembly according to claim 1, wherein the accumulating state is at least 20 seconds.

10. The curing assembly according to claim 1, wherein the first pressure plate assembly and the second pressure plate assembly each include a plate arranged in a parallel direction relative to the product stack.

11. The curing assembly according to claim 1, wherein only one of the first pressure plate assembly and the second pressure plate assembly is engaged with the product stack in both the accumulating state and the output state.

12. The curing assembly according to claim 1, wherein during an emptying mode, either (i) each of the first pressure plate assembly and the second pressure plate assembly are engaged with the product stack, or (i) only the second pressure plate assembly is engaged with the product stack.

13. The curing assembly according to claim 1, wherein the control assembly is configured to drive the first pressure plate assembly via a first motor and an associated first pressure plate timing belt, and the control assembly is configured to independently drive the second pressure plate assembly via a second motor and an associated second pressure plate timing belt.

14. The curing assembly according to claim 1, wherein the first pressure plate assembly is configured to be held in either (i) a hold mode in which a predetermined torque is applied to the first pressure plate assembly, or (ii) idled during an accumulating state.

15. A method of applying pressure to products for curing adhesive, the method comprising:

(i) feeding the products to a curing assembly to form a product stack;

(ii) engaging a leading edge of the product stack with a first pressure plate assembly at least during an initial stage of an accumulating state such that a first predetermined pressure is applied to the product stack;

(iii) engaging a trailing edge of the product stack with a second pressure plate assembly at least during a final stage of an output state such that a second predetermined pressure is applied to the product stack;

(iv) engaging an upper portion of the product stack with an overhead guide assembly, and guiding lateral portions of the product stack via a side guide assembly; and (v) discharging the products from the curing assembly.

16. The method according to claim 15, wherein the first pressure plate assembly and the second pressure plate assembly each include a plate arranged in a parallel direction relative to the product stack.

17. The method according to claim 15, further comprising driving the first pressure plate assembly out of contact with the product stack during the output state.

18. The method according to claim 15, further comprising positioning the second pressure plate assembly away from the product stack during the accumulating state.

19. The method according to claim 15, wherein a discharge assembly including at least one discharge belt is configured to discharge the products during step (iv) via engagement of the at least one discharge belt against the leading edge of the product stack.

20. The method according to claim 15, further comprising adjusting a pressure applied to the product stack via adding or removing products from the product stack held within the curing assembly, wherein the curing assembly defines a predetermined area for the product stack.

21. The method according to claim 15, further comprising applying a constant pressure to the product stack during a combined input-output state in which a constant number of products are fed and discharged to the curing assembly.

22. The method according to claim 15, further comprising driving the first pressure plate assembly forward via contact with an accumulating product stack.

* * * * *